United States Patent [19]

Zelmanovic et al.

[11] Patent Number: 6,114,173
[45] Date of Patent: *Sep. 5, 2000

[54] FULLY AUTOMATED METHOD AND REAGENT COMPOSITION THEREFOR FOR RAPID IDENTIFICATION AND CHARACTERIZATION OF RETICULOCYTES ERYTHROCYTES AND PLATELETS IN WHOLE BLOOD

[75] Inventors: David Zelmanovic, Monsey; Lynn Paseltiner, Monroe, both of N.Y.; Martin Sorette, Brighton, Mass.

[73] Assignee: Bayer Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/833,033

[22] Filed: Apr. 3, 1997

[51] Int. Cl.⁷ .................................................. G01N 33/48
[52] U.S. Cl. .................... 436/63; 436/8; 436/10; 436/17; 436/18; 436/66; 436/164; 436/166; 435/2; 252/408.1
[58] Field of Search .................................... 436/8, 10, 15, 436/17, 18, 63, 66, 164, 166, 172, 174; 435/2; 252/408.1

[56] References Cited

U.S. PATENT DOCUMENTS

| | | | |
|---|---|---|---|
| 3,684,377 | 8/1972 | Adams et al. | 356/36 |
| 3,883,247 | 5/1975 | Adams | 356/39 |
| 4,325,706 | 4/1982 | Gershman et al. | 435/6 |
| 4,336,029 | 6/1982 | Natale | 436/172 |
| 4,412,004 | 10/1983 | Ornstein et al. | 436/10 |
| 4,575,490 | 3/1986 | Ornstein et al. | 436/63 |
| 4,707,451 | 11/1987 | Sage, Jr. | 436/63 |
| 4,735,504 | 4/1988 | Tycko | 356/336 |
| 4,883,867 | 11/1989 | Lee et al. | 536/25.4 |
| 4,971,917 | 11/1990 | Kuroda | 436/63 |
| 4,981,803 | 1/1991 | Kuroda | 436/63 |
| 5,075,556 | 12/1991 | Fan et al. | 250/459.1 |
| 5,284,771 | 2/1994 | Fan et al. | 436/10 |
| 5,350,695 | 9/1994 | Colella et al. | 436/63 |
| 5,360,739 | 11/1994 | Fan et al. | 436/63 |
| 5,411,891 | 5/1995 | Fan et al. | 436/63 |
| 5,631,165 | 5/1997 | Chupp et al. | 436/43 |
| 5,830,764 | 11/1998 | Sorette | 436/63 |

OTHER PUBLICATIONS

H. Shapiro and S. Stephens, 1986, "Flow Cytometry of DNA Content Using Oxazine 750 or Related Laser Dyes with 633nm Excitation", *Cytometry*, 7:107–110.

*Primary Examiner*—Maureen M. Wallenhorst
*Attorney, Agent, or Firm*—Morgan & Finnegan, LLP

[57] ABSTRACT

The invention provides a very fast and reliable method and reagent composition for determining reticulocyte and erythrocyte counts, identification and characterization, as well as platelet counts, in a whole blood sample using fully automated hematology analyzers. The reagent composition includes a zwitterionic surfactant as sphering agent for reticulocytes and erythrocytes, an organic cationic dye, e.g., Oxazine 750, for staining the reticulocytes, and buffer solution components for maintaining a reagent pH of about 7.2 to 7.8, and an osmolarity of about 292±5. On the basis of the particular pH, ionic strength, and dye concentration, the reagent composition of the present method improves upon previous methods, thus allowing fully automated blood sample analyses to be completed in less than about 30 seconds, with only about a 20 second incubation of sample in the reagent solution before analysis. With such a rapid incubation time, the reagent mixture is passed through the sensing region of a flow cytometer, and the light scattered and absorbed by each cell is rapidly measured to provide accurate cell determinations and counts. The volume and hemoglobin concentration and content of each erythrocyte or reticulocyte are determined. Mean cell volume, mean corpuscular hemoglobin concentration, and mean cell hemoglobin of the reticulocytes and/or erythrocytes are calculated from the measured cell-by-cell volume and hemoglobin concentration.

39 Claims, 5 Drawing Sheets

PLT 386.66 x $10^3$/uL
MPV 8.65 fl
PCT 0.33 %
PDW 51.27 %

PLT 593.79 x $10^3$/uL
MPV 6.99 fl
PCT 0.42 %
PDW 56.07 %

FULLY AUTOMATED METHOD AND REAGENT COMPOSITION THEREFOR FOR RAPID IDENTIFICATION AND CHARACTERIZATION OF RETICULOCYTES ERYTHROCYTES AND PLATELETS IN WHOLE BLOOD

FIELD OF THE INVENTION

The present invention relates to fully automated hematology analysis methods and reagent compositions used therein for identifying and characterizing cells in samples of whole blood, and more particularly for (i) identifying reticulocytes and erythrocytes; (ii) identifying and distinguishing platelets; and (iii) simultaneously measuring the volume, hemoglobin concentration and hemoglobin content of large numbers of individual reticulocytes and erythrocytes, in a whole blood sample by light scatter and absorption flow cytometry techniques.

BACKGROUND OF THE INVENTION

In all higher animals, blood consists of an aqueous fluid part (the plasma) in which are suspended corpuscles of various kinds: the red blood cells (erythrocytes), the white blood cells (leukocytes) and the blood platelets. Plasma has a composition comprising roughly 90% water, 9% protein, 0.9% salts and traces of other materials such as sugar, urea, uric acid, and the like.

The cells or corpuscles of the peripheral blood (i.e. the blood outside of the bone marrow) are divided into two main groups: erythrocytes whose primary object is to transport oxygen, and leukocytes whose primary function relates to the immune system and the destruction of materials foreign to the body. In addition to these two main groups, the blood also contains the so-called blood platelets which are important in hemostasis.

The final stages of erythrocyte maturation occur after their release from the bone marrow while these cells are circulating in the peripheral blood. These young red cells, or "reticulocytes", have lost their nuclei, and thus, their ability to divide or to synthesize ribonucleic acid (RNA). Although these functions have ceased, reticulocytes are still metabolically active and are capable of synthesizing protein, taking up iron for the synthesis of heme, and carrying out the necessary metabolic reactions required to maintain an energy-rich state. These cells are usually most easily distinguished from mature erythrocytes by exposing them to solutions of cationic dyes which react with the anionic RNA in the reticulocytes and precipitate into a fine or coarse stained "reticulum" within the reticulocytes, which gives the reticulocytes their name.

Although reticulocytes normally comprise about 0.5 to 2 percent of the total red blood cell population, this percentage can change dramatically under abnormal conditions. For example, reticulocyte counts have been used for many years as a diagnostic aid in studying blood dyscrasias, as an index of red blood cell regeneration following hemorrhage, as well as for monitoring early toxicity in chemotherapy of certain malignant diseases.

Nucleic acids (RNA and DNA) are polyanions which can be stained with practically any cationic dye. The RNA in reticulocytes can be stained with only a few cationic dyes, including, for example, Brilliant Cresyl Blue (BCG), New Methylene Blue (NMB), Auramine O (AuO), Acridine Orange (AO), Thiazole Orange (TO), Oxazine 750, and Pyronine Y (PY). Among these dyes, only a sub-set can be made to penetrate the cells (and therefore stain) rapidly. The rate and degree of staining of reticulocytes depend upon the extracellular concentration of the dye, the rate of penetration of the dye through the reticulocyte membrane, and the strength of the specific binding constant between the cationic dye and the reticulocyte RNA. The latter two properties are different, and are not easily predictable for each dye, so that trial and error are necessary to discover useful reticulocyte stains.

Several semi-automated methods are available which can be used for counting the percentage of reticulocytes in an anticoagulated sample of whole blood using fluorescent based methods and systems. In such methods, a diluent containing an organic cationic dye, such as AO, AuO or TO, is used to stain the RNA within the reticulocytes. The dye penetrates the cell membrane and binds to the RNA and usually precipitates a "reticulum" within each reticulocyte. The amount of the signal from stained RNA is roughly proportional to the RNA content. After proper staining, a fluorescence flow cytometer (rather than an absorption flow cytometer), equipped with the proper excitation light source (typically an argon ion laser emitting at 488 nm), and emission detection system, can be used to determine the percentage of reticulocytes in the effluent.

Although fluorescent cytometric methods and fluorescent dyes have been used in the art to differentiate reticulocytes in whole blood samples, there is a dearth of very rapid, accurate, and reliable cytometric methods using fully automated scatter/absorption flow cytometry techniques for determining reticulocyte, red blood cell and platelet counts, and for assessing further parameters of reticulocytes and red blood cells. However, the present invention, which comprises a method and reagent designed for rapid whole blood sample analysis via light scatter and absorption fully automated flow cytometry, provides the art with a needed and highly advantageous blood analysis method and reagent for use with fully automated hematology systems. The invention speeds up the process of blood cell analysis to allow more samples to be tested and analyzed and to provide a much faster turnaround time for processing and, ultimately, informing clinicians, physicians, and patients of the results.

A difficulty in monitoring reticulocyte counts with a flow cytometer is the problem of differentiating between reticulocyte detection signals, mature red blood cell signals, and system noise. The stained strands of RNA are numerous in young reticulocytes, and generate signals of relatively large magnitude when detected by a flow cytometer. However, more mature cells contain less stained RNA and generate smaller signals which may be masked by the noise of the flow cytometer measuring system. A need exists for fast and accurate methods and reagents used therefor for rapidly identifying reticulocytes and simultaneously measuring the volume, hemoglobin concentration and hemoglobin content of reticulocytes and erythrocytes in a whole blood sample by light scatter and absorption flow cytometry techniques in fully automated systems, which rapidly process samples.

Illustrative methods for differentiating reticulocytes in whole blood samples using fluorescent dyes and fluorescent-based flow cytometric methods, which are unlike the present invention and which frequently require many seconds to several minutes of sample incubation prior to analysis, are disclosed in the patent literature. For example, U.S. Pat. No. 3,684,377 to Adams and Kamentsky discloses a dye composition for differential blood analysis including an aqueous solution of AO, and having a pH factor and osmolality within normal physiological ranges for human blood. The dye composition can be used for counting reticulocytes by measuring the presence or absence of a fluorescence signal with an erythrocyte scatter signal.

U.S. Pat. No. 3,883,247 to Adams discloses a similar method to that of Adams and Kamentsky using a dye composition including AO having a concentration of between $10^{-6}$ and $10^{-5}$ grams per ml.

U.S. Pat. No. 4,336,029 to Natale discloses a reagent composition comprising an aqueous solution of the dye AO, citrate ion and paraformaldehyde at a pH of about 7.4 and an isotonic osmolality. The concentrations of the various ingredients were selected to maximize dye uptake of the reticulocytes and platelets, and resulted in dye uptake being achieved within 2–5 minutes of mixing the blood sample and reagent composition. An automated method for detection of platelets and reticulocytes utilizing the Natale reagent is disclosed in U.S. Pat. No. 4,325,706 to Gershman et al.

In the reagent disclosed in U.S. Pat. No. 4,707,451 to Sage, Jr., reticulocytes are stained with thioflavin T or chrysaniline. A whole blood sample was found to be effectively stained by mixing a 25 $\mu$l aliquot of the dye in an isotonic saline solution (0.2 mg/ml) with 10 $\mu$l of anticoagulated whole blood with the mixture incubated for about 7 minutes.

U.S. Pat. No. 4,883,867 to Lee et al. discloses a dye composition for staining RNA or DNA. The staining composition includes TO as the preferred dye compound. The reticulocytes are stained in a minimum time of 30 minutes.

A reagent for reticulocyte counting with flow cytometric techniques is described in U.S. Pat. No. 4,971,917 to Kuroda and contains a carbonate salt to reduce the non-specific staining of the mature erythrocytes by the dye, e.g. AuO, to prevent the mature erythrocytes from being erroneously counted as reticulocytes when analyzed by fluorescence flow cytometry.

U.S. Pat. No. 4,981,803 describes a reagent for reticulocyte counting which comprises two solutions, namely a stock solution for staining in which a dye AuO is dissolved in a non-aqueous solvent and a buffer solution which satisfies the optimum staining conditions.

Another reticulocyte staining reagent for fluorescence flow cytometric techniques including AuO is disclosed in U.S. Pat. No. 4,985,176 to Kuroda et al. This patent discloses an incubation time of the reagent and sample for fluorescent analysis from between the wide range of 30 seconds and 20 minutes.

Quaternized AO derivatives for quantifying reticulocytes are described in U.S. Pat. No. 5,075,556 to S. Fan and G. Fischer. The Fan et al. reagent contains $10^{-6}$ gram per ml of an AO derivative in a buffer solution including paraformaldehyde and potassium oxalate and stains reticulocytes to enable the quantitative fluorescence flow cytometric analysis of reticulocytes in a blood sample.

None of the above-mentioned reagents contain a sphering agent to prevent orientational noise problems as discussed below, and none permit the simultaneous determination of other diagnostically significant parameters such as volume and hemoglobin concentration of the reticulocytes and erythrocytes on a cell-by-cell basis. Moreover, several of the above-described methods require sample preparation, and reaction or incubation time with reagent solution, which are not suitable for a very rapid method for use in fully automated systems that involve quicker and faster rapid sample processing times.

Shapiro and Stephens disclose the use of Oxazine 750 for the determination of DNA content by flow cytometry in "Flow Cytometry of DNA Content Using Oxazine 750 or Related Laser Dyes With 633 nm Excitation", *Cytometry*, Vol. 7, pp. 107–110 (1986). The cells are stained by 10 $\mu$M to 30 $\mu$M of Oxazine 750, and are fixed by the addition of ethanol for the DNA determination. Shapiro and Stephens claim that Oxazine 750 does not appear to stain RNA within the cells. Moreover, such protocols with Oxazine 750 do not permit reticulocyte counting or simultaneous determination of other diagnostically significant red blood cell parameters such as volume and hemoglobin concentration on a cell-by-cell basis.

U.S. Pat. Nos. 4,575,490 and 4,412,004 to Kim and Ornstein teach a method and reagent for the elimination of orientational noise in the measurement of the volume of red blood cells in a flow cytometer. The disclosed method involves isovolumetric sphering of unstained red blood cells to eliminate any orientational differences between the cells to permit more precise and accurate measurement of cell volume. Each red blood cell is converted from a biconcave shape to a perfect sphere by a surfactant sphering agent. A "buffering" protein and/or an aldehyde fixing agent are disclosed to be required for use with the sphering agent to prevent lysis of the erythrocytes. The anionic surfactant sphering agents in the reagents described by Kim and Ornstein cannot be used with reticulocyte stains because they react rapidly with and precipitate the cationic dyes used to stain and precipitate the reticulum.

U.S. Pat. Nos. 5,360,739 and 5,411,891 to S. S. Fan et al. disclose methods and reagent compositions for reticulocyte determination using cationic dye and fluorescence/scatter flow cytometry analysis.

U.S. Pat. No. 4,735,504 to Tycko discloses the red blood cell channel of the TECHNICON H•1™ system, a flow cytometer which provides a fully automated method and means for determining the individual and mean erythrocyte volumes (MCV), and individual and mean corpuscular hemoglobin concentrations (MCHC) of the erythrocytes in an anticoagulated whole blood sample. In this method, the red blood cells in a two microliter aliquot of a whole blood sample are first diluted, and then isovolumetrically sphered using methods known in the art. After a twenty second incubation period, these cells are passed, essentially one at a time, through the illuminated measurement zone within the red cell channel of the analyzer. The method of Tycko does not distinguish between reticulocytes and non-reticulocytes and does not determine separately the diagnostically significant parameters of the reticulocytes and erythrocytes, such as volume and hemoglobin concentration on a cell-by-cell basis.

The present invention affords significant advantages to the art by providing an improved and more rapid method of blood cell determination which requires no manual sample preparation time and which allows an incubation time of less than about twenty seconds in reaction solution on fully automated hematology analyzer systems prior to blood sample analysis. In addition, the invention affords reproducible, reliable and accurate results using scatter/absorption flow cytometry techniques. Such results are attained demonstrably faster than can be obtained with existing scatter/absorption flow cytometry methods.

SUMMARY OF THE INVENTION

Accordingly, it is a principal object of the present invention to provide an improved and rapid (i.e., about 20 seconds or less reaction time) method and reagent composition for differentiating reticulocytes, red blood cells, and platelets from other cells in a whole blood sample by absorption flow cytometry techniques using fully automated sample analysis and high-speed automated hematology analyzers.

Another object of the invention is to provide rapid and sensitive method and reagent composition used therein for enumerating reticulocytes, red blood cells and platelets in a whole blood sample employing fully automated absorption flow cytometry analyzers in which no manual sample preparation, and thus, no additional sample preparation time, are required prior to the automated blood sample analysis.

A further object of the invention is to provide a fully automated and rapid method and reagent composition therefor for the simultaneous sphering of red blood cells and reticulocytes and staining of reticulocytes and for obtaining reticulocyte counts and indices and platelet counts within only a few seconds, compared with other automated methods of blood cell analysis employing scatter/absorption flow cytometry.

A further object of the invention is to provide a fully automated and rapid method and reagent composition therefor to determine reticulocyte and red blood cell indices, such as mean cellular volume, hemoglobin concentration and hemoglobin content in a whole blood sample by absorption and scattered light flow cytometry. The invention further provides the distributions of the above cellular parameters.

Still yet another object of the invention is to provide a method and reagent composition as above for simultaneously discriminating between and counting each of the red blood cells, reticulocytes, and platelets within a blood sample, and for determining the volume, hemoglobin content, hemoglobin concentration, mean erythrocyte volume, and mean corpuscular hemoglobin concentration of each red blood cell type determined from measurements on a cell-by-cell basis.

DESCRIPTION OF THE DRAWINGS

The above and other objects and significant advantages of the invention are believed to be made clear by the following detailed description thereof taken in conjunction with the accompanying drawings wherein:

FIGS. 1A and 1B depict cytograms presenting the scatter versus absorption patterns associated with whole blood sample analysis. The cytogram regions corresponding with various cell types and report screen areas are specifically identified in FIG. 1A. The regions include: red blood cells (RBCs), reticulocytes (retics), platelets (PLTs) and coincidence signals. Coincidence signals result from the presence of two or more particles in the counting region at one time. FIGS. 1C and 1D depict histograms showing the distribution of platelet volumes within the samples. FIG. 1A represents a normal blood sample; FIG. 1B represents an abnormal blood sample.

FIG. 4A shows a comparison of red blood cell counts using the method in accordance with the invention and a standard automated method, for example, the BAYER H•3™ Hematology Analyzer. FIG. 4B shows a comparison of platelet counts obtained using the rapid automated method of the invention versus a standard automated method. For FIGS. 4A and 4B, ten normal samples were run in duplicate in each method. The least-squares equation and the correlation coefficient (r) are presented on the graphs.

DETAILED DESCRIPTION OF THE INVENTION

Figure 1A:
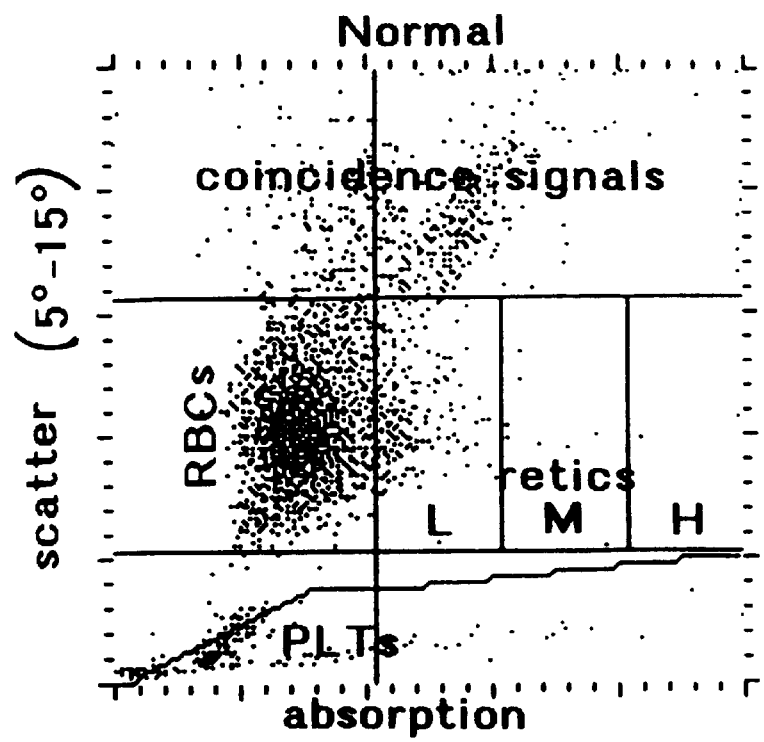
FIGS. 1A–1D show the results of scatter/absorption flow cytometry analyses as performed in accordance with the present invention.

In the area of hematology analysis, there is an ever-present need for more rapid assays and analysis methods for determining absolute and percent red blood cell and reticulocyte counts, and for determining platelet counts in a blood sample drawn for testing.

Semi-automated hematology analyzers as used in the art routinely provide sample data after a blood sample containing blood cells is mixed with an appropriate reagent solution to form a reagent mixture (i.e., a reaction suspension), either within or outside of the analyzer system. After a period of incubation of the reagent mixture, the mixture is analyzed in a hematology analysis device. Thus, sample preparation and incubation are limiting factors contributing to the length of time needed to analyze a blood sample in semi-automated hematology devices.

For fully automated, high-speed analyzers, such as the TECHNICON H• System series of analyzers, for example, more rapid, automated hematology and whole blood sample analysis methods are needed for accurate and reliable integration and processing in the faster systems. A novel method which requires no off-line, manual sample preparation and is thus essentially a one-step process of sample analysis which occurs within the automated analyzer is afforded by the present invention. The method and reagent used therefor eliminate manual sample preparation and processing times and thus significantly and advantageously decrease the overall blood cell identification and determination times, i.e., by at least an order of magnitude, when compared with those of other scatter/absorption methods in the art.

In an embodiment of the invention, a rapid method is provided for determining reticulocyte, red blood cell and platelet counts and for determining reticulocyte and red blood cell indices and parameters using fully automated analyzers based on measurements of light scatter and absorption. The use of light scatter and absorption methodology for the very rapid automated sample analysis as described herein provides an improved process to the art which routinely employs fluorescence-based methodology.

The method of the invention comprises the use of a reticulocyte staining reagent which comprises a cationic dye at a concentration effective to stain reticulocytes in a whole blood sample for enumeration and characterization of the cells within about 5 to 60 seconds, preferably, within about 20 to 50 seconds, and more preferably, within about 20 to 30 seconds or less, of the initial reaction with an aliquot of the whole blood sample. In accordance with the invention, a blood sample can be analyzed in an automated hematology analyzer in about 30 seconds, which includes approximately 20 seconds of reaction time of sample in the reagent composition and approximately 10 seconds of counting time, with less than approximately 0.1 second of mathematical analysis time.

The simplicity and rapidity of the method are advantageous for the skilled practitioner. Because no sample preparation is involved, even the least skilled personnel may operate the fully automated analyzers, employ the method of the invention, and obtain accurate and reliable blood cell counts and indices. In addition, many more samples can be analyzed in the same period of time that was previously needed to perform fewer blood sample analyses using semi-automated systems; for example, in accordance with the present invention, blood sample analysis occurs within less than about 20 to 30 seconds in a fully automated system versus at least about 150 seconds for a semi-automated method.

The aqueous reagent composition involved in the method comprises a buffer to maintain the pH of the reaction mixture at a value that will prevent non-specific staining of mature red blood cells from interfering with the reticulocyte and erythrocyte enumeration and characterization analyses. Blood samples may be anti-coagulated as conventionally known in the art. The reagent further comprises a sphering agent, which is preferably a zwitterionic surfactant as described herein, to enable the determination of reticulocyte indices; the reagent is also optimized with respect to osmolarity of the buffered reaction solution.

Those skilled in the art will appreciate that not all cationic compounds are capable of penetrating intact red cell (and reticulocyte) membranes, and the nature of the anions which necessarily accompany the cations can affect whether or not the cationic compound penetrates rapidly, slowly, or not at all. Hydrophobic molecules generally penetrate red cell membranes faster than hydrophilic molecules, and small molecules generally penetrate membranes faster than large molecules. Only a sub-set of salts or buffers mixed with those cationic dyes which can stain reticulocytes permit rapid staining; that is, the "right" dye with the "wrong" buffer can take an excessive amount of time to stain reticulocytes. Again, trial and error are necessary to discover useful formulations of reticulocyte staining mixtures. Thus, despite various "rules" which can be used as guides, it is difficult to predict, a priori, whether and under which conditions, any particular cationic dye may rapidly penetrate and stain reticulocytes.

The fully automated apparatus for performing blood sample analyses using the method and reagent of the invention generally comprises 1) blood and reagent metering devices to provide the proper volume of each of the reaction components; 2) a means for adequately mixing the components together; 3) a reaction chamber; and 4) a means for transferring the mixture to the measurement device. The measurement device comprises a means for providing a metered flow of the cell-containing reaction mixture through a flow cell for counting and enumeration. In general, light from a Helium-Neon laser or laser diode is incident upon the flow cell and this light is interrupted by the passage of blood cells through the flow cell. The blood cells scatter light as they intercept it, and, in the case of stained reticulocytes, absorb light as well.

The measurement device includes three optical detectors. Two of the detectors detect light scattered at 1°–3° and 4°–20°, respectively, preferably at 2°–3° and 5°–15°, respectively, from the axis of incidence. The third detector determines the fraction of light absorbed. The signals from the three detectors are analyzed by a computer, which uses Mie Scattering Theory-derived tables to convert the signals into cell volume, hemoglobin concentration and hemoglobin content data for each cell which passes through the flow cell. The computer also displays a cytogram of the 5°–15° scatter versus absorption for the cell suspension and uses mathematical algorithms to distinguish and differentiate among red blood cells, reticulocytes, platelets and coincidence signals.

Figure 1B:
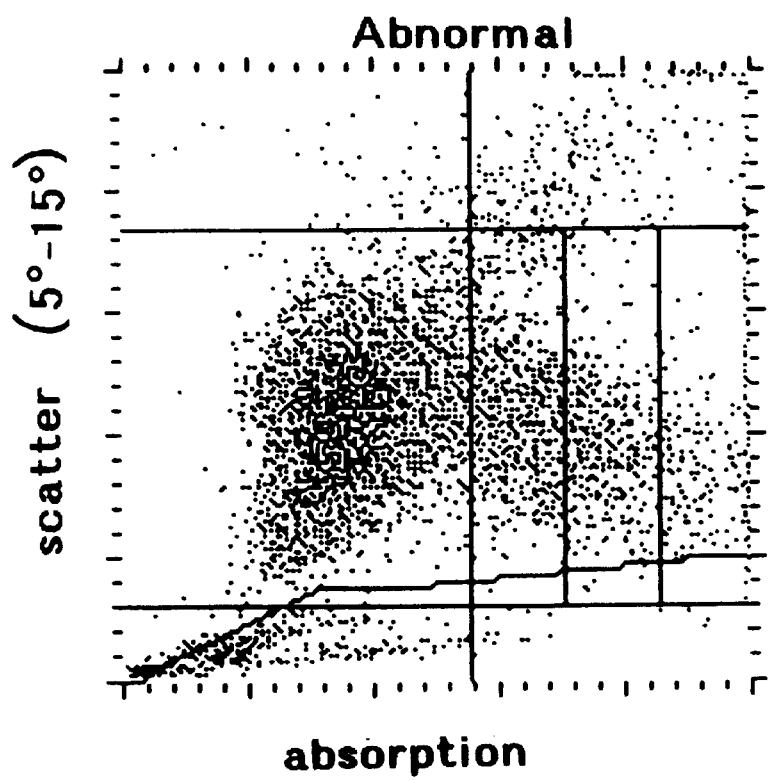
Figure 1C:
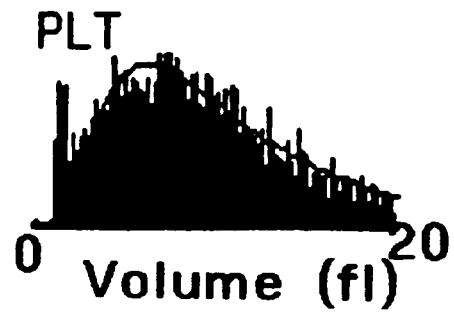
Figure 1D:
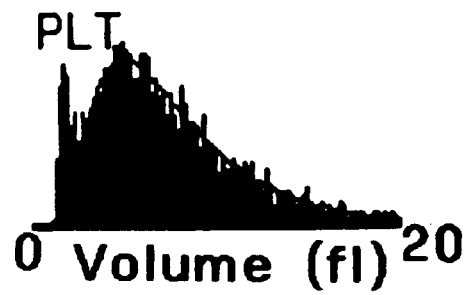

For example, report screens obtained from the above-described analysis are shown in FIGS. 1A and 1B. One of the screens reports the data obtained for a blood sample having a normal percentage of reticulocytes (i.e., 1.4); the second screen reports the data obtained for an abnormal blood sample in which the percentage of reticulocytes is 11.0. The reports include the reticulocyte indices. For FIGS. 1A and 1B, the reported results, which correlate with the cytograms, are as follows:

For FIG. 1A:

| SAMPLE | RETICS |
|---|---|
| CHCM 30.04 g/dl | CHCM 27.43 g/dL |
| MCV 93.86 fl | MCV 115.60 fl |
| MCH 27.60 pg | MCH 30.98 pg |
| HDW 2.41 g/dl | HDW 2.38 g/dl |
| RDW 13.03% | RDW 17.61% |
| RBC 5.19 × $10^6$/µL | |
| RETIC 71.97 × $10^9$/L | |
| POS 251 | |
| NEG 17860 | |
| % POS 1.39% | |
| L 96.81% | |
| M 2.79% | |
| H 0.40% | |

For Fig. 1B:

| | |
|---|---|
| CHCM 30.01 g/dl | CHCM 26.81 g/dL |
| MCV 96.94 fl | MCV 113.15 fl |
| MCH 28.35 pg | MCH 29.56 pg |
| HDW 4.02 g/dl | HDW 3.76 g/dl |
| RDW 20.21% | RDW 18.53% |
| RBC 2.89 × $10^6$/µL | |
| RETIC 318.13 × $10^9$/L | |
| POS 1769 | |
| NEG 14280 | |
| % POS 11.02% | |
| L 60.15% | |
| M 29.79% | |
| H 10.06% | |

These reported results for FIGS. 1A and 1B are as follows: SAMPLE=the total number of cells analyzed; RETICS=cells counted as reticulocytes; CHCM=Cellular Hemoglobin Concentration Mean, which measures the same cellular property as MCHC or Mean Cellular Hemoglobin Concentration; MCV=Mean Cellular Volume (of red blood cells); MCH=Mean Cellular Hemoglobin; HDW=Hemoglobin Distribution Width (a measure of the variability of cellular hemoglobin concentration with a sample); RDW=Red(blood cell) Distribution Width; RBC=Red Blood Cell Count; RETIC=Reticulocyte Count; POS=number of reticulocytes counted; NEG=number of red blood cells counted; % POS= reticulocyte percentage in sample; L, M, H=percentage of low, medium, and high-staining reticulocytes; PLT=Platelet count; MPV=Mean Platelet Volume; PCT=Platelet Crit (the percentage of sample volume occupied by platelets); PDW= Platelet Distribution Width (the distribution of platelet volumes within the sample).

An illustrative measurement device and system suitable for the analyses of the invention is as described in U.S. Pat. No. 4,735,504 to Tycko, which is incorporated by reference herein. It is to be understood that the Tycko method and system may be modified as necessary by those in the art for performance of the improved, rapid method of the invention.

To utilize Tycko's method, a light source which emits monochromatic light in a region where hemoglobin is very transparent is required; typically a light source like a red helium neon (HeNe) laser, or a laser with even longer wavelength. This means that if that wavelength is also to be used for the absorption measurement, the dye must be a blue dye with a strong absorption of red light. The dye Oxazine 750 serves as a preferred dye and use in the improved and rapid absorption/scatter flow cytometric method of the invention for determining reticulocyte RNA concentration, reticulocyte cell count, platelet count and mature red cell and reticulocyte volume and hemoglobin content on a cell-by-cell basis.

More particularly, the fundamental concept of flow cytometry is essentially the passing of cells, one at a time, through a specific sensing region. Typically, by means of hydrodynamic focusing, single cells are passed through the sensing zone, which consists of a focused light source and a detection system for the measurement of scattered and absorbed light.

The effect that a particle has on the light it intercepts can be detected in a number of ways. In general, the particle has a refractive index which is different from that of the medium in which it is suspended. The refractive index, n, consists of two parts: the real part, $n_r$, and the so-called imaginary part, $n_i$. Non-zero values of $n_i$ are associated with light absorption. A particle will therefore scatter and absorb light with which it is illuminated through a range of angles, and with varying intensities, that depend upon that refractive index difference, the particle's size, its shape and any internal variations in refractive index and structure, as well as upon the wavelength of the illuminating light. (For homogeneous spheres, Mie Scattering Theory provides a complete description of the distribution and intensities of scattered light).

As stated above, a particle may also absorb some of the incident light. In the latter case, a portion of the absorbed light may or may not be re-emitted as fluorescence, typically at a longer wavelength than the wavelength of the absorbed light. These and other effects can be measured with light detectors arranged to measure different angular intervals of scattered light, unscattered light, fluorescent light and the fraction of light absorbed by the particle.

When particles are as small as blood cells, typically less than 15 micrometers in diameter, the number of photons in the illuminating beam affected by their passage at high speed (typically hundreds to thousands of widely-spaced cells per second) can be very small, especially when compared with the number of photons per second falling on the illuminated part of the suspension stream, and compared with the background illumination of an absorption detector. Therefore, the limits of sensitivity of detection of small particular differences between particles depends critically on the photon flux (which depends at least on the intrinsic "brightness" of the light source) and how large the perturbations of the photon flux are that are produced by other small and large differences between particles.

The main sources of interfering noise in absorption and scatter flow cytometry signals can be quite different for each kind of signal. To a first order approximation, the magnitudes of scatter and absorption signals from stained or unstained cells are very strongly influenced by shape or orientation of the cells from which the signals arise. As an extreme example, the native biconcave shape of human erythrocytes has a profound effect on the absorption and scatter signals they generate; such an effect is larger than the small absorption signals of typical classically stained reticulocytes. A description of scatter/absorption flow cytometric analyses for reticulocyte determination is described in U.S. Pat. Nos. 5,350,695 and 5,438,003 to G. Colella et al., the contents of which are incorporated by reference herein.

As noted above, only a small sub-set of cationic dyes selectively stains reticulocytes, and only a smaller sub-set of these dyes rapidly penetrates reticulocytes. The concentration of cationic dye compound combined with the optimal pH and ionic strength of the reagent composition used in the method of the invention achieve the rapid staining of reticulocyte RNA and sample analysis in seconds. This allows reticulocyte, red cell and platelet analyses by fully automated flow cytometry to be performed in less than about 20 to 30 seconds after the blood sample and the reagent composition employed in the method are mixed together, thus contributing to the speed of the present invention and its successful and accurate performance in fully automated procedures. The method and reagent of the invention allow blood sample analyses at least an order of magnitude faster than current scatter/absorption flow cytometry methods in the art. By contrast, former reticulocyte RNA staining procedures require at least several minutes for sample and reagent mixture and incubation.

The present invention significantly improves upon former methods by achieving a significant reduction in reaction time between a blood sample and the presently described reagent composition with which it is mixed prior to automated hematology analysis. The inventive discovery of the combination of increased cationic dye concentration, reduction of the pH of the reagent composition and an optimal osmolarity range used in the method was found to reduce the reaction time of the blood sample with the reagent composition, which collectively comprise the reagent mixture for analysis. This novel combination of parameters favored the staining of RNA in reticulocytes over the non-specific staining of hemoglobin in mature red blood cells as described hereinbelow.

Interestingly, increasing the dye concentration in the composition did not, by itself, reduce the reaction time of the blood sample mixed with the reaction medium. This was because within the first 30 seconds, mature red blood cells as well as reticulocytes significantly bound to the dye (e.g., Oxazine 750) at the higher concentrations required for use in the present invention. With a longer time of incubation of blood sample in the reaction medium (e.g., over 30 seconds), the binding of dye by the mature red cells declined. Thus, the longer reaction times of other methods were required not only to increase the binding of the cationic dye to RNA, but also to decrease the binding of dye to the cellular hemoglobin of mature red blood cells, thus causing non-specific staining of red blood cells. Such non-specific staining reduces the distinction between red cells and reticulocytes with respect to absorption signals.

In spite of the foregoing, the present method and composition used therein were able to achieve a fast reaction time without the adverse effect of non-specific staining by cells other than reticulocytes. Affinity of the dye for red blood cells was reduced while adequate affinity for reticulocyte RNA was maintained by the invention within a 20 second or less reaction time period by the above-described reduction of pH (e.g., reducing the pH of the reaction medium from approximately 8.1 to approximately 7.4) combined with an increased cationic dye concentration. In accordance with the invention, the increased hydrogen ion concentration of the reagent composition may reduce the affinity of hemoglobin for the positively-charged dye compound.

Moreover, it was determined that a reduction of the ionic strength of the reaction medium favored the staining of RNA over red cell hemoglobin, thereby reducing the reaction time. The reduced ionic strength may favor the binding of RNA to the positively-charged dye rather than to other ionic constituents in the reaction mixture.

In another aspect of the invention, the binding of cationic dye, e.g., Oxazine 750, to mature red blood cells was reduced, without adverse effects on RNA binding, by converting hemoglobin to its oxidized (Met) form in the presence of nucleophiles such as azides ($N_3^-$), e.g., sodium azide, or cyanate ($OCN^-$) ion, e.g., sodium cyanate. See Table 1 and FIG. 2. As a result, as little as about one-fifth of the amount of dye used in the absence of such nucleophiles can be used in this embodiment of the present invention. Without wishing to be bound by any particular theory, it is possible that the conformational structural change to hemoglobin associated with the oxidized form may reduce the affinity of hemoglobin for the positively charged dye component of the reagent composition. As a general guide, nucleophiles are used at a concentration of about approximately 20 mM, provided that there is a 1:1 ratio of $N_3^-$ or $OCN^-$ ions to home sites. Because reagents which include both nucleophiles and dyes such as Oxazine 750 are not typically stable during storage, the reagents can be stored in two parts, which when added together yield the required final concentrations of components. An illustrative example of such a two-part reagent system is shown in Table 1:

TABLE 1

| Reagent Component | Part 1 (Per liter) | Range (Per liter) | Part 2 (Per liter) | Range (Per liter) |
|---|---|---|---|---|
| TRIS | 0.81 g | 0.7–0.9 g | 0.81 g | 0.7–0.9 g |
| TRIS-HCl | 6.83 g | 6.0–8.0 g | 6.83 g | 6.0–8.0 g |
| NaCl | 6.40 g | 5.25–7.30 g | 5.82 g | 4.67–6.72 g |
| Proclin 300 | 0.25 ml | 0.15–0.35 ml | — | — |
| $NaN_3$ or NaOCN | — | — | 1.303 g | 1.10–1.50 g |
| TDAPS* | 16.5 ml | 8.2–22.0 ml | — | — |
| Oxazine 750** | 2.2 ml | 1.8–6.6 ml | — | — |
| Deionized $H_2O$ | 950 ml | — | 950 ml | — |

*Amount of stock solution. 1 mg/ml TDAPS (tetradecyl-N,N-dimethyl-3-ammonio-1-propanesulfonate) in distilled $H_2O$.
**Amount of stock solution. 14.82 mg Oxazine 750 dye per 4.81 ml dimethyl formamide.

Figure 2:
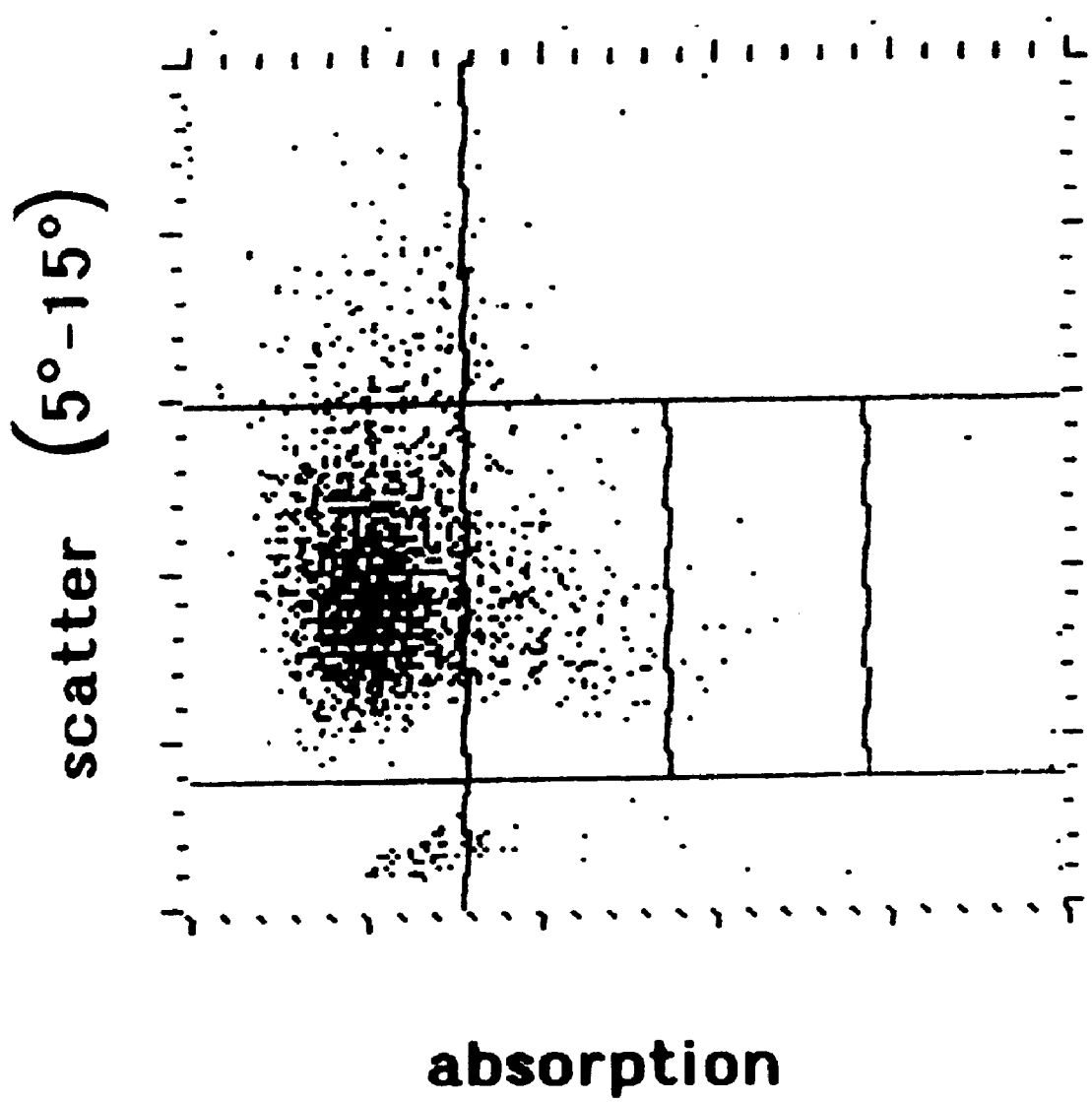
FIG. 2 presents a scatter/absorption cytogram displaying typical results for a normal blood sample analyzed in accordance with the invention using $NaN^3$ in a reagent formulation as shown in Table 1 herein. The cytogram descriptors are as set forth in FIGS. 1A and 1B and as described hereinbelow.

The cytogram of FIG. 2 is representative of a normal sample analyzed using the sodium azide formulation presented in Table 1. The reaction time for the analysis was 20 seconds. In the FIG. 2 cytogram, the parameters, which are defined above for FIGS. 1A and 1B, are as follows:

| SAMPLE | RETICS |
|---|---|
| CHCM 27.40 g/dl | CHCM 24.13 g/dL |
| MCV 96.22 fl | MCV 119.13 fl |
| MCH 25.74 pg | MCH 27.84 pg |
| HDW 2.71 g/dl | HDW 3.62 g/dl |
| RDW 14.31% | RDW 17.50% |
| RBC 4.15 × $10^6/\mu L$ | |
| RETIC 62.94 × $10^9/L$ | |
| POS 276 | |
| NEG 17917 | |
| % POS 1.52% | |

As described above, investigations into improving and accelerating the process of absorption/scatter flow cytometry analysis, and developing the method and reagent used therein to detect reticulocytes, erythrocytes and platelets resulted in the present, extremely rapid method which involved staining of the reticulum of reticulocytes by a cationic dye without a requirement for sample preparation for particular use with fully automated hematology analyzers. In addition, in the improved and rapid absorption method of the invention, the isovolumetric sphering of red cells was used to eliminate orientational noise. By using isovolumetric sphering and scatter/absorption methods, reticulocyte and mature red cell volume and hemoglobin could be simultaneously measured and quantified on a cell-by-cell basis using a reagent which also selectively stained reticulocytes. Those skilled in the art will appreciate that if the sphering is complete, and not isovolumetric, but has some known factor X of isotonicity, then by using Tycko's method with a correction by 1/X for volume and a correction by X for protein, e.g., hemoglobin concentration, original values can be calculated.

In the reagent solution employed for use in the current method, a zwitterionic surfactant was used as a red cell and reticulocyte sphering agent, since it is fully compatible with cationic dyes and does not cause precipitation of the dye out of the reagent solution. Non-limiting examples of such zwitterionic surfactants include alkyl amido betaines or alkyl betaines, such as lauramidopropylbetaine (LAB), cocoamidopropylbetaine (CAPB), and cocoamidosulfobetaine (CASB). Other suitable zwitterionic surfactants include: tetradecyl-N,N-dimethyl-3-ammonio-1-propanesulfonate (TDAPS) and N-dodecyl-N, N-dimethyl-3-ammonio-1-propanesulfonate (DDAPS). TDAPS and DDAPS are the preferred sphering agents because they give the most stable sample preparation. In accordance with the invention, the use of red cell sphering-effective amounts of these types of surfactants and the reagent specifications as described herein obviate the need for protein buffering or fixatives in the reagent mixture to delay red cell lysis.

For the reagent solution of the present invention and to isovolumetrically sphere the reticulocytes and red blood cells within a blood sample, the concentration of the sphering agent in the reagent is from about 3.0 μg/ml to about 20 μg/ml, preferably about 4.0 to about 15 μg/ml, and more preferably about 4.1 to about 11.0 μg/ml. TDAPS is a preferred zwitterionic surfactant sphering agent. The sphering agent is preferably present in an amount of from about 12 μg/ml to about 87.5 μg/ml of LAB; from about 4.1 μg/ml to about 11.0 μg/ml of TDAPS; from about 49.3 μg/ml to about 148 μg/ml of DDAPS; from about 8.8 μg/ml to about 17.5 μg/ml of CAPB; or from about 12.5 μg/ml to about 15 μg/ml of CASB.

For optimal operativity of the improved method, a buffer solution is preferably used for maintaining a particular pH of the reaction mixture, i.e., about 7.2 to 7.8, preferably, 7.3 to 7.5, more preferably 7.4, as is an organic cationic dye for staining the reticulocytes. The preferred dye compound is Oxazine 750 (available from Excitron, Inc. of Dayton, Ohio), which is a blue absorption dye having the structure:

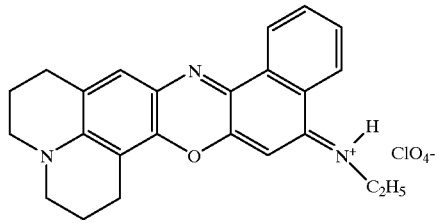

More particularly, the reagent solution for use in the method of the invention may include one or more of the following constituents: TRIS (Tris[hydroxymethyl]-aminomethane); TRIS-HCl (Tris[hydroxymethyl]- aminomethane-hydrochloric acid); an alkali metal chloride salt, e.g., NaCl, KCl and the like, to facilitate the penetration of dye through the red blood cell membrane; and, if desired, an antimicrobial compound to retard microbial growth. Nonlimiting examples of suitable antimicrobials include Proclin 150 (2-methyl-4-isothiazolin-3-one) and Proclin 300 (5-chloro-2-methyl-4-isothiazolin-3-one) (Rohm & Haas); Germall 115 (N,N'-methylenebis[N'-(1-(hydroxymethyl)-2, 5-dioxo-4-imidazolidinyl] urea) (Sutton Laboratories); Dowacil 200 (1-(3-chloroallyl)-3,5,7-triaza-1-azoniaadamantane chloride) (Dow Chemical); and Bronopol 2-bromo-2-nitropropane-1, 3-diol ($C_3H_6BrNO_4$), (Angus Chemical Company). Proclin 300 is a preferred antimicrobial for use in the reagent composition employed in the present invention. Also included in the composition is a zwitterionic surfactant, e.g., TDAPS (N-Tetradecyl-N,N-Dimethyl-3-Ammonio-1-Propane Sulfonate); and a cationic dye, e.g., Oxazine 750.

An illustrative reagent composition/solution of the present invention and suitable for use in the present methods is shown in Table 2, with suitable concentration ranges for each component and the amounts per liter for each component provided. The final pH of the composition is about 7.4, and the final osmolarity is adjusted with either NaCl or TDAPS solution to 292±5 mOsm. The final pH is adjusted to the appropriate pH, preferably, pH 7.4, by the dropwise addition of 1 N HCl or 1 N NaOH.

TABLE 2

| Constituents in Reagent Solution | Concentration Range of Components Amount/liter | Amount per Liter (Preferred) |
| --- | --- | --- |
| TRIS | 0.7–0.9 g | 0.806 g |
| TRIS-HCl | 6.0–8.0 g | 6.83 g |
| NaCl | 5.25–7.30 g | 6.40 g |
| PROCLIN 300 | 0.15–0.35 ml | 0.25 ml |
| TDAPS (Stock Solution)* | 4.1–11.0 ml | 8.25 ml |
| Oxazine 750 (Stock Solution)** | 2.2–6.6 ml | 3.3 ml |
| Deionized Water | To volume | 950 ml |

*1 mg/ml TDAPS (N-tetradecyl-N,N-dimethyl-3-ammonio-1-propane sulfonate) in distilled water.
**14.82 mg Oxazine 750 dye per 4.81 ml dimethylformamide.

In general, the reagent solution may be formulated to maintain the pH of the reagent composition at between about 7.2 to about 7.8, with 7.4 as a preferred pH value, with an osmolarity of about 250 mOsm to about 320 mOsm, preferably, about 287 mOsm to 297 mOsm, more preferably about 292±5 mOsm.

In the reagent solutions having the pH and osmolality ranges as described above, the concentration of cationic dye, e.g., Oxazine 750, required for RNA staining is in the range of from about 6 to about 20 µg/ml, preferably about 6.5 µg/ml to about 19.5 µg/ml, more preferably about 9.0 µg/ml to about 10.5 µg/ml. The buffer enhanced penetration results in the dye staining RNA in the reticulocytes in about 20 to 30 seconds or less. The concentration of dye in the reagent of the method minimizes non-reticulocyte staining of mature erythrocytes which leads to a good signal separation from the noise background. Such rapid staining, due to the optimized conditions of the reagent, obviates incubating the blood sample in the reagent for more than about 20 seconds prior to sample analysis, and makes the method highly advantageous, acceptable and compatible for fully automated hematology methods.

The method and reagent composition may be used to identify and discriminate reticulocytes in a whole blood sample using the technique of scatter/absorption flow cytometry. The method in its broadest application includes adding an aliquot of whole blood to the reagent composition as described for use in the method. With less than about a 20 second incubation period after mixing, the sample/reagent mixture is passed, one cell at a time, through a specific sensing region of the flow cytometer. By means of hydrodynamic focusing, single cells are passed through the sensing zone, where they are illuminated by a focused light source having a suitable illumination wavelength. At least two scattered light signals and at least one absorption signal are measured for the cells on a cell-by-cell basis. From these measurements, the reticulocytes can be distinguished from the erythrocytes.

In accordance with the present invention, platelets are distinguished from reticulocytes and red blood cells in a sample by size and refractive index, which separates their signals from those of larger, more refractile red blood cells.

When the reaction mixture (comprising the whole blood sample and reagent composition/solution) is passed through the sensing region of a flow cytometer, the light is scattered through two angular intervals and absorbed by each cell is measured, such that the erythrocytes can be distinguished from reticulocytes, and the volume and hemoglobin concentration of each reticulocyte or erythrocyte can be determined. Platelets occupy a distinct region of scatter/scatter/absorption "space"; the signals in this region are counted as platelets. The number of reticulocytes and erythrocytes, and the hemoglobin content, mean cell volume, mean corpuscular hemoglobin concentration, and mean cell hemoglobin of the reticulocytes or erythrocytes are calculated from the measured cell-by-cell volume and hemoglobin concentration.

More particularly, to carry out the method, 2 µl aliquots of whole blood were aspirated by the automated hematology analysis instrument, e.g., the TECHNICON H•3 Hematology System, modified with respect to analysis software. The modifications included the aspiration of whole blood, which was subsequently mixed with reagents on-system rather than the aspiration of a diluted sample that had already undergone about 5–90 minutes of off-line (off-system) reaction. Also, the modified analysis provided absolute red blood cell and reticulocyte counts, as well as percent reticulocytes, rather than merely percent reticulocytes. Further, the method in accordance with the invention provided platelet counts, values for mean platelet volume and platelet-volume histograms. These parameters are not provided in the reticulocyte channel of the H•3 Hematology System.

In accordance with the present invention, the sample aliquots were automatically mixed with the present reagent composition and permitted to stand for about 20 seconds. Thereafter, the mixed sample was passed through the flow cell and was then exposed to either a helium-neon laser source or a laser-diode source for red cell reticulocyte and platelet analysis.

The invention accordingly comprises the methods and reagents hereinafter described in the Examples, the scope of the invention being indicated in the claims.

EXAMPLES

The following Examples set forth the method and reagent composition used therein for the identification of reticulocytes, red blood cells, and platelets, and for the characterization of reticulocytes and red blood cells using absorption/scatter flow cytometry techniques. Standard, commercially-available, reagent-grade materials were used whenever possible.

Example 1
Rapid, Automated Scatter and Absorption Measurements for Distinguishing Reticulocytes and Erythrocytes in a Whole Blood Sample Using the Method and Reagent Composition of the Present Invention Oxazine 750 dye was stored in a 2.96 mg/ml N,N-dimethylformamide stock solution. A working reagent was created by adding the dye stock to a buffer solution containing the preferred components and at the preferred concentrations presented in Table 2. The final osmolarity and pH of the working reagent used in this study were 292 mmol/kg and 7.4, respectively.

Figure 3:
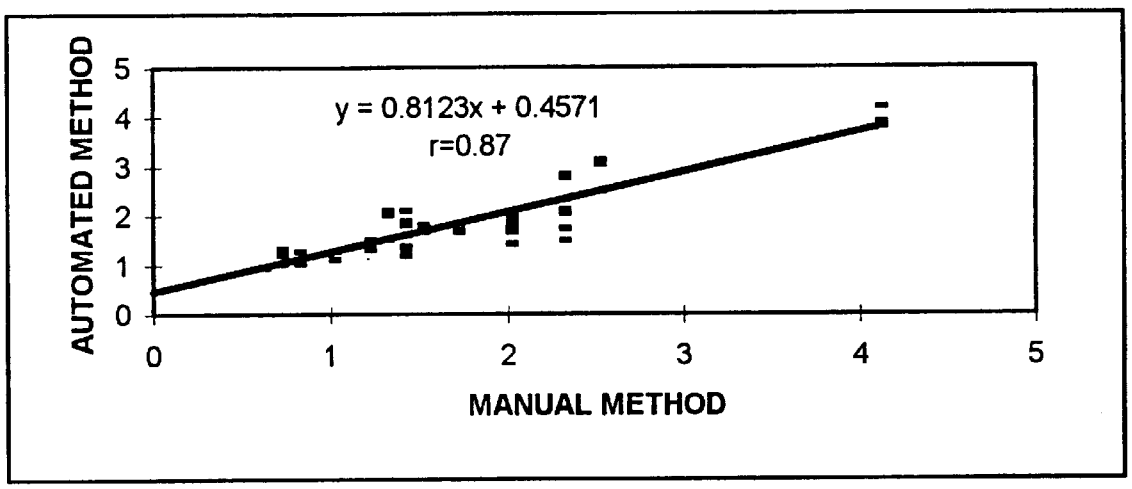
FIG. 3 shows the highly correlated results of comparative studies employing the rapid automated method and composition of the invention and a manual method of whole blood cell analysis to perform reticulocyte determinations using scatter/absorption flow cytometry. The least squares equation and the correlation coefficient (r) are presented on the graph.

In this example, for each sample, 2 $\mu$l of whole blood aspirated by the automated system was mixed with 625 $\mu$l of the Table 2 reagent composition for 20 seconds at room temperature and the cells in the mixture were then analyzed by flow cytometry as described herein. Ten normal-donor blood samples ("normals") and ten randomly-selected hospital patient blood samples ("abnormals") were analyzed for percent reticulocytes by the present method and by a manual method. Each sample was analyzed by the automated instrument in duplicate (n=40). The results are graphically depicted in FIG. 3. As shown in FIG. 3, the mean reticulocyte percentage was 1.8 for the automated method versus 1.7 for the manual method. The correlation coefficient was 0.87. The small difference between the means and the high correlation coefficient demonstrates that the 20-second automated method provides accurate values for reticulocyte percentages for both normal and abnormal sample populations.

At the completion of the analysis, the raw data were displayed in the form of a Red Scatter v. Red Absorption cytogram, e.g., FIGS. 1A and 1B. Distinct cell populations were clearly observed based on their particular scatter and absorption signals. In these cytogram plots, the erythrocyte population falls within the region labeled "RBCs" in FIG. 1A. These cells show high scatter signals and low cell absorption signals. The reticulocyte population falls within the region labeled "retics", including the regions labeled "L", "M" and "H". These cells are distinguishable from the mature erythrocytes due to the higher absorption signals from their Oxazine 750-stained RNA. The platelet population lies in the region labeled "PLTs", and the coincidence signals are in the appropriately labeled region. The platelets have relatively low scatter signals when compared with the reticulocytes.

Based on the absorption separation between mature erythrocytes and reticulocytes, the reticulocyte count of a patient sample may be determined by creating electronic "windows" which define the ranges of scattered light and absorption which identify reticulocytes and erythrocytes. The number of reticulocytes, mature erythrocytes and platelets falling within each "window" are determined so that the percentages of the reticulocytes, erythrocytes and platelets present in the total cell population is then calculated. The absolute red blood cell count, reticulocyte count and platelet count are determined as well, based on the known dilution factors associated with the automated instrumentation.

The reference percentage of reticulocytes in each sample was determined using the manual microscopic procedure recommended by the National Committee for Clinical Laboratory Standards (NCCLS). In this procedure, a small volume, e.g., 100 $\mu$l, of whole blood was mixed with an equal volume of new methylene blue dye and allowed to react for about 15 minutes at room temperature. This mixture was then applied to a microscope slide in the form of a smear and the percentage of reticulocytes in the sample was counted upon visualization using a microscope. The microscope was equipped with a 100× oil immersion objective and a 10× ocular. A minimum of 1000 cells were counted for each sample using a Miller disc inserted in the ocular of the microscope to improve counting precision. Any red cell containing two or more particles of blue material after staining was labeled a reticulocyte.

Figure 4A:
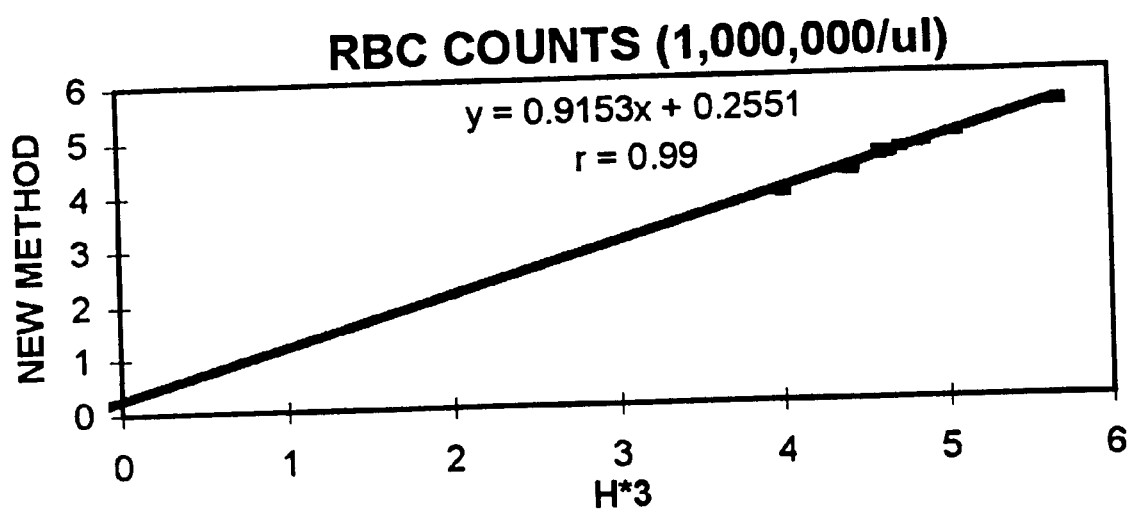
FIGS. 4A and 4B show the results of red blood cell (4A) and platelet (4B) determinations using the rapid automated method as described herein.
Figure 4B:
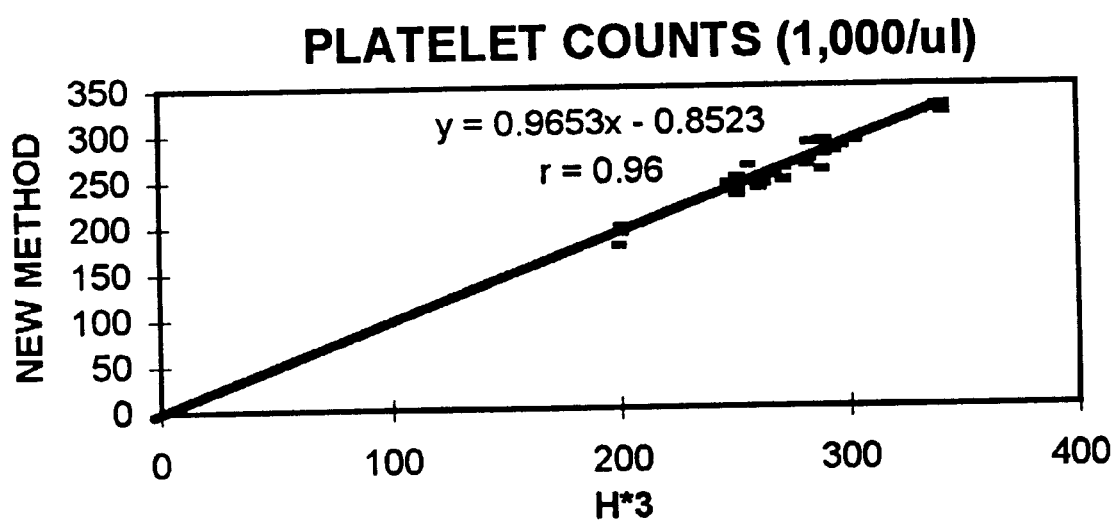

Example 2
Red Blood Cell and Platelet Determinations Obtained from the Method in Accordance With the Present Invention Experiments were performed to demonstrate that the rapid automated method of the present invention provided accurate red blood cell and platelet counts as well as reticulocyte counts. Ten fresh samples, (i.e., samples that were used less than about eight hours after collection) were taken from normal donors and analyzed by both the new method of the invention and a standard hematology analyzer, e.g., the BAYER H•3™ Hematology Analyzer. Each blood sample was run in duplicate for a total of twenty aspirations for each method. The results of these analyses are presented in FIGS. 4A and 4B. The results show that the counts obtained by the new and rapid method are highly correlated with those obtained using a standard method.

Example 3
Correction of Absorption Data for Pseudo-absorption

The detection optical subsystem collects both the scattered and unscattered light from cells passing through the laser beam in the flowcell. Cells scatter light into all directions. The relatively Hi-numerical aperture (NA) lens in the optical system, which is described in U.S. Pat. Nos. 5,350,695 and 5,438,003 to G. Colella et al., accepts the light that is scattered into a cone that is centered on the optical axis with a half angle of up to 19.5 degrees. Thus, the light that is scattered into angles greater than 19.5 degrees is lost. As a result, when attempting to measure cellular absorption, completely non-absorbing cells "appear" to absorb up to a few percent of the incident light, i.e., pseudo-absorption. The measured absorption can be represented as follows:

$$\text{Absorption Signal} = \text{Pseudo-Absorption} + \text{Hemoglobin Absorption} + \text{Dye Absorption}$$

The pseudo-absorption signal of a mature red blood cell is typically of the same magnitude as the actual absorption signal from a stained reticulocyte. This reduces the degree of separation of the stained reticulocytes from the unstained red blood cells on the absorption cytogram. The signal to noise ratio of the absorption channel can be improved by correcting the signal to remove the pseudo-absorption and hemoglobin absorption components from each red cell and reticulocyte absorption signal. The amount of pseudo-absorption and hemoglobin absorption can be calculated for any given cell by using the well-known Mie light scattering theory described in the aforenoted Tycko patent. The scattering cross-section for the angular interval 19.5° to 180° plus the hemoglobin absorption component, $S_3$, can be calculated as follows:

$$S_3 = \pi a^2 Q_{ext} - S(\lambda, n_s, \Theta_3, \Delta\Theta_3; V, HC)$$

where a is the radius of the sphered cell, $\lambda$ is the excitation (or illuminating) wavelength, $n_s$ is the refractive index of the sample stream and sheath, $Q_{ext}$ is the extinction efficiency of the cell, and for the case of pseudo-absorption, $\Theta_3=0°$, and $\Delta\Theta_3=19.5°$. $S_3$ values have been tabulated for all expected values of V and HC.

The pseudo-absorption correction is made as follows: the V and HC must first be determined from the two scattering signals from a cell from the scatter-scatter cytogram as described in Tycko. $S_3$ is then found in the look-up table entry for the measured V and HC, and subtracted from the value measured by the absorption channel. The result is the actual absorption due to staining of the cell. The measured absorption signal can be adjusted using the following relation, to leave only the dye absorption for each cell:

$$\begin{aligned}\text{Dye} \atop \text{Absorption} &= \text{Absorption} \atop \text{Signal} - \text{Hemoglobin} \atop \text{Absorption} - \text{Pseudo-} \atop \text{Absorption} \\ &= \text{Absorption Signal} - S_3\end{aligned}$$

For all data, the adjusted value is substituted for the raw data parameter prior to thresholding and flagging. Any objects whose red scatter parameters do not appear on the V-HC map are ignored in the data analysis scheme. These data are then redisplayed with the red scatter v. absorption cytogram reflecting the corrected values.

In view of the above, it will be seen that the several objects of the invention are achieved, and other advantageous results obtained.

As various changes can be made in the above constructions and methods without departing from the scope of the invention, it is intended that all matter contained in the above description, or shown on the accompanying drawings, shall be interpreted as illustrative, not in a limiting sense. For instance, fractionated samples of blood can be processed in a similar way.

The contents of all patent applications, issued patents, articles, references, texts, and the like, as cited herein are hereby incorporated by reference in their entirety to more fully describe the state of the art to which the present invention pertains.

What is claimed is:

1. A rapid method for blood sample analysis, wherein reticulocyte, erythrocyte and platelet subclasses of blood cells are identified, quantified and differentiated from other subclasses of blood cells in a whole blood sample by light scatter and absorption flow cytometry using an automated hematology analyzer, comprising the steps of:

(a) preparing a reaction mixture comprising an aliquot of said blood sample admixed with an aqueous reagent composition, said reagent composition comprising a reagent solution containing a cationic dye in an amount of from about 9 to about 10.5 µg/ml, a zwitterionic surfactant as sphering agent in an amount of from about 4 µg/ml to about 11 µg/ml, and a buffer or buffer mixture for maintaining a pH of about 7.3 to about 7.5 and for providing an increased hydrogen ion concentration of the reagent solution to reduce the affinity of hemoglobin in the blood sample for the cationic dye; said reagent solution having an osmolarity of about 292+/−5 mOsm, thereby providing an reduced ionic strength of the composition to favor binding of RNA in reticulocytes to the cationic dye over non-specific staining of mature red blood cells in the whole blood sample; wherein said reagent composition and said whole blood sample aliquot are not preincubated or reacted with each other in said reaction mixture for more than about 20 to 30 seconds prior to performing said sample analysis on said automated analyzer; and further wherein the reagent solution provides an enhanced penetration of the dye staining of reticulocyte RNA within about 20 to 30 seconds following mixture of said blood sample aliquot and said reagent composition;

(b) passing said mixture of (a) substantially one cell at a time through an area of focused optical illumination;

(c) detecting and measuring light scattered into two angle intervals and the light absorbed by each cell; and (d) differentiating and obtaining both absolute counts and percents of cells of said reticulocyte, erythrocyte and platelet subclasses, at least in part on the basis of measured magnitudes of said scattered and absorbed light; wherein said whole blood sample is analyzed in from about 5 to about 60 seconds in said automated hematology analyzer.

2. The method according to claim 1, wherein said cationic dye is present in said reagent composition of (a) in an amount of 10 µg/ml to 10.5 µg/ml.

3. The method according to claim 1, wherein said cationic dye is Oxazine 750 having the formula:

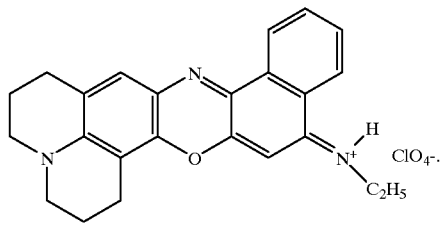

4. The method according to claim 1, wherein the buffer or buffer mixture has a pH of 7.4.

5. The method according to claim 1, wherein said zwitterionic surfactant sphering agent in said reagent composition of (a) is selected from the group consisting of lauramidopropylbetaine, N-tetradecyl-N, N-dimethyl-3-ammonio-1-propanesulfonate, N-dodecyl-N, N-dimethyl-3-ammonio-1-propanesulfonate, cocoamidopropylbetaine and cocoamidosulfobetaine.

6. The method according to claim 5, wherein said surfactant is N-tetradecyl-N, N-dimethyl-3-ammonio-1-propanesulfonate.

7. The method according to claim 1, wherein said surfactant is present in the reagent composition an amount of approximately 8 µg/ml.

8. The method according to claim 1, wherein said osmolarity is 292 mOsm.

9. The method according to claim 1, wherein said reagent composition of (a) further comprises an alkali metal salt.

10. The method according to claim 9, wherein said reagent composition of (a) further comprises sodium chloride or potassium chloride.

11. The method according to claim 1, wherein said reagent composition of (a) further comprises an antimicrobial compound.

12. The method according to claim 11, wherein said antimicrobial compound is selected from the group consisting of 2-methyl-4-isothiazolin-3-one; 5-chloro-2-methyl-4-isothiazolin-3-one; (N,N'-methylenebis[N'-(1-(hydroxymethyl)-2,5-dioxo-4-imidazolidinyl] urea; 1-(3-chloroallyl)-3,5,7-triaza-1-azoniaadamantane chloride; and 2-bromo-2-nitropropane-1,3-diol ($C_3H_6BrNO_4$).

13. The method according to claim 1, wherein said blood sample is analyzed in from about 20 to about 50 seconds.

14. The method according to claim 1, wherein said blood sample is analyzed in about 30 seconds.

15. The method according to claim 1, wherein said detection and measurement (c) includes collecting said light scattered and absorbed through a collection optics which includes an aperture, and (d) includes correcting absorption signal magnitude which includes a pseudo-absorption component to remove the pseudo-absorption component due to light scattered outside of the aperture of the collection optics.

16. The method according to claim 1, further comprising:
    (e) determining number, volume, hemoglobin concentration, and RNA concentration of said reticulocytes or erythrocytes based on measured magnitudes of said scattered and absorbed light.

17. The method according to claim 1, wherein said optical illumination in (b) has an excitation wavelength in the red region of the spectrum.

18. The method according to claim 1, wherein said reagent composition of (a) further comprises at least one nucleophile.

19. The method according to claim 18, wherein said nucleophile is an azide ($N_3^-$) or cyanate ($OCN^-$) ion.

20. The method according to claim 18, wherein said nucleophile is present in said reagent composition at a concentration of about 20 mM.

21. The method according to claim 1, wherein in (c) the two angle intervals are 1 to 3 degrees and 4 to 20 degrees, respectively.

22. The method according to claim 21, wherein in (c) the two angle intervals are 2 to 3 degrees and 5 to 15 degrees, respectively.

23. A reagent composition for rapidly identifying and characterizing reticulocyte, erythrocyte and platelet subclasses of blood cells in a whole blood sample in about 60 seconds or less in an automated hematology analyzer, comprising in aqueous admixture: a cationic dye in an amount of from about 9 μg/ml to 10.5 μg/ml; a zwitterionic surfactant as sphering agent in an amount of from about 4 μg/ml to about 11 μg/ml; and a buffer for maintaining a pH of said composition of about 7.3 to 7.5; said reagent composition having an osmolarity of about 292+/−5 mOsm; wherein said whole blood sample is not preincubated or premixed with said reagent composition for more than about 20 to 30 seconds prior to performing a blood sample analysis; and further wherein said whole blood sample admixed with said reagent composition is analyzed in from about 5 to about 60 seconds in said automated hematology analyzer.

24. The reagent composition according to claim 23, wherein said cationic dye is Oxazine 750 having the formula:

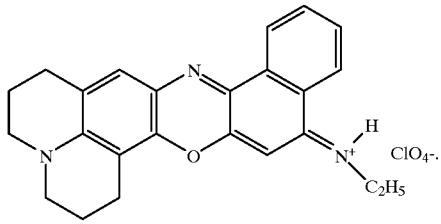

25. The reagent composition according to claim 23, wherein said pH is 7.4.

26. The reagent composition according to claim 23, wherein said osmolarity is 292 mOsm.

27. The reagent composition according to claim 23, wherein said surfactant sphering agent is selected from the group consisting of lauramidopropylbetaine, N-tetradecyl-N, N-dimethyl-3-ammonio-1-propanesulfonate, N-dodecyl-N, N-dimethyl-3-ammonio-1-propanesulfonate, cocoamidopropylbetaine and cocoamidosulfobetaine.

28. The reagent composition according to claim 27, wherein said surfactant is N-tetradecyl-N, N-dimethyl-3-ammonio-1-propanesulfonate.

29. The reagent composition according to claim 23, wherein said surfactant is present in an amount of approximately 8 μg/ml.

30. The reagent composition according to claim 23, further comprising an alkali metal salt.

31. The reagent composition according to claim 30, wherein said alkali metal salt is sodium chloride or potassium chloride.

32. The reagent composition according to claim 23, further comprising an antimicrobial compound.

33. The reagent composition according to claim 32, wherein said antimicrobial compound is selected from the group consisting of 2-methyl-4-isothiazolin-3-one; 5-chloro-2-methyl-4-isothiazolin-3-one; (N,N'-methylenebis[N'-(1-(hydroxymethyl)-2,5-dioxo-4-imidazolidinyl] urea; 1-(3-chloroallyl)-3,5,7-triaza-1-azoniaadamantane chloride; and 2-bromo-2-nitropropane-1, 3-diol ($C_3H_6BrNO_4$).

34. The reagent composition according to claim 23, wherein said blood sample is analyzed in from about 20 to 50 seconds.

35. The reagent composition according to claim 23, wherein said blood sample is analyzed in about 30 seconds.

36. The reagent composition according to claim 23, further comprising at least one nucleophile in an amount effective to reduce binding of the cationic dye to mature red blood cells in the whole blood sample.

37. The reagent composition according to claim 36, wherein said nucleophile is an azide ($N_3^-$) or cyanate ($OCN^-$) ion.

38. The reagent composition according to claim 36, wherein said nucleophile is present at a concentration of about 20 mM.

39. The reagent composition according to claim 23, wherein said cationic dye is present in an amount of 10 μg/ml to 10.5 μg/ml.

* * * * *